(12) United States Patent
Joshi et al.

(10) Patent No.: US 9,259,582 B2
(45) Date of Patent: Feb. 16, 2016

(54) SLOT ANTENNA FOR AN IMPLANTABLE DEVICE

(75) Inventors: Himanshu Joshi, Houston, TX (US); David L. Thompson, Houston, TX (US); Jared Brandon Floyd, Ferndale, WA (US); Eric Y. Chow, Houston, TX (US); Jonathan D. Rowell, San Antonio, TX (US)

(73) Assignee: CYBERONICS, INC., Houston, TX (US)

( * ) Notice: Subject to any disclaimer, the term of this patent is extended or adjusted under 35 U.S.C. 154(b) by 954 days.

(21) Appl. No.: 13/098,279

(22) Filed: Apr. 29, 2011

(65) Prior Publication Data

US 2012/0276854 A1 Nov. 1, 2012

(51) Int. Cl.
*H04B 5/00* (2006.01)
*A61N 1/372* (2006.01)
*H01Q 1/38* (2006.01)
*H01Q 21/08* (2006.01)
*H01Q 21/20* (2006.01)
*H01Q 1/27* (2006.01)
*H01Q 1/52* (2006.01)
*H01Q 7/00* (2006.01)
*H01Q 9/04* (2006.01)
*H01Q 13/10* (2006.01)
*H01Q 21/30* (2006.01)
*A61N 1/375* (2006.01)
*H02J 7/02* (2006.01)

(52) U.S. Cl.
CPC ............ *A61N 1/37229* (2013.01); *H01Q 1/273* (2013.01); *H01Q 1/38* (2013.01); *H01Q 1/521* (2013.01); *H01Q 7/00* (2013.01); *H01Q 9/045* (2013.01); *H01Q 13/106* (2013.01); *H01Q 21/08* (2013.01); *H01Q 21/205* (2013.01); *H01Q 21/30* (2013.01); *A61N 1/375* (2013.01); *H02J 7/025* (2013.01); *Y10T 29/49016* (2015.01)

(58) Field of Classification Search
USPC .............. 455/41.1, 41.2, 575.1, 575.5, 575.6, 455/575.7; 607/32, 33, 36, 60, 61; 343/767, 343/768, 770, 700 MS
See application file for complete search history.

(56) References Cited

U.S. PATENT DOCUMENTS

| 4,030,480 A | 6/1977 | Meyer |
| 4,075,632 A | 2/1978 | Baldwin et al. |
| 4,127,110 A | 11/1978 | Bullara |
| 4,305,397 A | 12/1981 | Weisbrod et al. |

(Continued)

OTHER PUBLICATIONS

International Application No. PCT/US2012/032007, International Search Report and Written Opinion of the International Searching Authority dated Sep. 13, 2013, 13 pages.

*Primary Examiner* — Tuan A Tran

(57) ABSTRACT

An implantable medical device may include a case which houses components of the implantable medical device. The implantable medical device may include an inductive coil coupled to a rechargeable battery. The inductive coil may be operative to inductively couple to an external coil and to transfer energy from the external coil to the rechargeable battery to recharge the rechargeable battery. The implantable medical device may include a cutout formed in the case of the implantable medical device and filled with a dielectric material. The cutout may be operative to reduce eddy currents in the case during recharge of the rechargeable battery. The implantable medical device may include a slot antenna disposed within the case. The slot antenna may be operative to communicate with an external device through the cutout in the case.

14 Claims, 9 Drawing Sheets

(56) References Cited

U.S. PATENT DOCUMENTS

| | | |
|---|---|---|
| 4,414,979 A | 11/1983 | Hirshorn et al. |
| 4,441,498 A | 4/1984 | Nordling |
| RE32,361 E | 2/1987 | Duggan |
| 4,800,899 A | 1/1989 | Elliott |
| 4,823,812 A | 4/1989 | Eshel et al. |
| 5,035,231 A | 7/1991 | Kubokawa et al. |
| 5,050,605 A | 9/1991 | Eydelman et al. |
| 5,058,581 A | 10/1991 | Silvian |
| 5,109,853 A | 5/1992 | Taicher et al. |
| 5,117,825 A | 6/1992 | Grevious |
| 5,168,871 A | 12/1992 | Grevious |
| 5,246,000 A | 9/1993 | Ellis et al. |
| 5,313,953 A | 5/1994 | Yomtov et al. |
| 5,314,453 A | 5/1994 | Jeutter |
| 5,330,518 A | 7/1994 | Neilson et al. |
| 5,336,245 A | 8/1994 | Adams et al. |
| 5,350,411 A | 9/1994 | Ryan et al. |
| 5,373,852 A | 12/1994 | Harrison et al. |
| 5,375,596 A | 12/1994 | Twiss et al. |
| 5,383,912 A | 1/1995 | Cox et al. |
| 5,402,788 A | 4/1995 | Fujio et al. |
| 5,456,698 A | 10/1995 | Byland et al. |
| 5,494,030 A | 2/1996 | Swartz et al. |
| 5,558,618 A | 9/1996 | Maniglia |
| 5,562,714 A | 10/1996 | Grevious |
| 5,629,678 A | 5/1997 | Gargano et al. |
| 5,630,835 A | 5/1997 | Brownlee |
| 5,697,958 A | 12/1997 | Paul et al. |
| 5,720,770 A | 2/1998 | Nappholz et al. |
| 5,735,887 A | 4/1998 | Barreras, Sr. et al. |
| 5,766,232 A | 6/1998 | Grevious et al. |
| 5,782,891 A | 7/1998 | Hassler et al. |
| 5,788,692 A | 8/1998 | Campbell et al. |
| 5,800,494 A | 9/1998 | Campbell et al. |
| 5,840,148 A | 11/1998 | Campbell et al. |
| 5,861,019 A | 1/1999 | Sun et al. |
| 5,873,840 A | 2/1999 | Neff |
| 5,902,251 A | 5/1999 | vanHooydonk |
| 5,928,145 A | 7/1999 | Ocali et al. |
| 5,951,594 A | 9/1999 | Kerver |
| 5,963,132 A | 10/1999 | Yoakum |
| 5,967,986 A | 10/1999 | Cimochowski et al. |
| 6,009,350 A | 12/1999 | Renken |
| 6,009,878 A | 1/2000 | Weijand et al. |
| 6,041,256 A | 3/2000 | Michel |
| 6,073,050 A | 6/2000 | Griffith |
| 6,115,634 A | 9/2000 | Donders et al. |
| 6,161,049 A | 12/2000 | Rudie et al. |
| 6,167,312 A | 12/2000 | Goedeke |
| 6,169,925 B1 | 1/2001 | Villaseca et al. |
| 6,175,768 B1 | 1/2001 | Arndt et al. |
| 6,176,856 B1 | 1/2001 | Jandak et al. |
| 6,190,382 B1 | 2/2001 | Ormsby et al. |
| 6,192,279 B1 | 2/2001 | Barreras, Sr. et al. |
| 6,201,993 B1 | 3/2001 | Kruse et al. |
| 6,240,317 B1 | 5/2001 | Villaseca et al. |
| 6,261,247 B1 | 7/2001 | Ishikawa et al. |
| 6,275,737 B1 | 8/2001 | Mann |
| 6,277,113 B1 | 8/2001 | Berube |
| 6,308,101 B1 | 10/2001 | Faltys et al. |
| 6,308,102 B1 | 10/2001 | Sieracki et al. |
| 6,379,300 B1 | 4/2002 | Haubrich |
| 6,393,327 B1 | 5/2002 | Scribner |
| 6,398,710 B1 | 6/2002 | Ishikawa et al. |
| 6,456,256 B1 | 9/2002 | Amundson et al. |
| 6,463,329 B1 | 10/2002 | Goedeke |
| 6,477,425 B1 | 11/2002 | Nowick et al. |
| 6,485,462 B1 | 11/2002 | Kriesel |
| 6,505,072 B1 | 1/2003 | Linder et al. |
| 6,516,227 B1 | 2/2003 | Meadows et al. |
| 6,556,169 B1 * | 4/2003 | Fukuura et al. ........ 343/700 MS |
| 6,561,975 B1 | 5/2003 | Pool et al. |
| 6,574,510 B2 | 6/2003 | Von Arx et al. |
| 6,610,054 B1 | 8/2003 | Edwards et al. |
| 6,631,290 B1 | 10/2003 | Guck et al. |
| 6,675,810 B2 | 1/2004 | Krag |
| 6,682,480 B1 | 1/2004 | Habib et al. |
| 6,708,065 B2 | 3/2004 | Von Arx et al. |
| 6,805,667 B2 | 10/2004 | Christopherson et al. |
| 6,894,616 B1 | 5/2005 | Forster |
| 6,922,591 B2 | 7/2005 | Single |
| 6,924,773 B1 | 8/2005 | Paratte |
| 7,042,357 B2 | 5/2006 | Girvin et al. |
| 7,043,307 B1 | 5/2006 | Zelickson et al. |
| 7,064,725 B2 * | 6/2006 | Shtrikman et al. ............ 343/770 |
| 7,092,763 B1 | 8/2006 | Griffith et al. |
| 7,146,861 B1 | 12/2006 | Cook et al. |
| 7,149,578 B2 | 12/2006 | Edvardsson |
| 7,191,013 B1 | 3/2007 | Miranda et al. |
| 7,203,549 B2 | 4/2007 | Schommer et al. |
| 7,209,792 B1 | 4/2007 | Parramon et al. |
| 7,212,866 B1 | 5/2007 | Griffith |
| 7,235,096 B1 | 6/2007 | Van Tassel et al. |
| 7,281,314 B2 | 10/2007 | Hess et al. |
| 7,286,877 B2 | 10/2007 | Daum |
| 7,399,280 B2 | 7/2008 | Liu et al. |
| 7,429,255 B2 | 9/2008 | Thompson |
| 7,432,723 B2 | 10/2008 | Ellis et al. |
| 7,483,732 B2 | 1/2009 | Zhong et al. |
| 7,483,752 B2 | 1/2009 | Von Arx et al. |
| 7,554,493 B1 | 6/2009 | Rahman |
| 7,561,921 B2 | 7/2009 | Phillips et al. |
| 7,577,476 B2 | 8/2009 | Hochman et al. |
| 7,695,435 B2 | 4/2010 | Benson et al. |
| 7,729,766 B2 | 6/2010 | Toy et al. |
| 7,860,476 B1 | 12/2010 | Karr et al. |
| 7,904,167 B2 | 3/2011 | Klosterman et al. |
| 7,907,091 B2 * | 3/2011 | Zhang ................... 343/700 MS |
| 7,983,760 B2 | 7/2011 | Ginggen et al. |
| 8,253,640 B2 * | 8/2012 | Kitayoshi et al. ............. 343/767 |
| 8,442,643 B2 | 5/2013 | Toy et al. |
| 8,565,891 B2 * | 10/2013 | Mumbru et al. ................ 607/60 |
| 8,599,086 B2 * | 12/2013 | Wong et al. ................... 343/767 |
| 8,725,263 B2 | 5/2014 | Yamamoto et al. |
| 2002/0095195 A1 | 7/2002 | Mass et al. |
| 2005/0113886 A1 | 5/2005 | Fischell et al. |
| 2005/0222633 A1 * | 10/2005 | Edvardsson .................... 607/36 |
| 2006/0028784 A1 | 2/2006 | Brendel |
| 2006/0247712 A1 | 11/2006 | Fuller et al. |
| 2007/0043399 A1 | 2/2007 | Stevenson et al. |
| 2007/0123949 A1 | 5/2007 | Dabney et al. |
| 2007/0273606 A1 | 11/2007 | Mak et al. |
| 2008/0033500 A1 | 2/2008 | Strother et al. |
| 2008/0091242 A1 | 4/2008 | Kamath et al. |
| 2008/0198082 A1 * | 8/2008 | Soler Castany et al. ...... 343/770 |
| 2008/0316112 A1 * | 12/2008 | Zhang ................... 343/700 MS |
| 2009/0228075 A1 | 9/2009 | Dion |
| 2009/0248112 A1 * | 10/2009 | Mumbru et al. ................ 607/60 |
| 2010/0060431 A1 | 3/2010 | Stevenson et al. |
| 2010/0082080 A1 | 4/2010 | Mateychuk |
| 2010/0109966 A1 | 5/2010 | Mateychuk et al. |
| 2010/0114205 A1 | 5/2010 | Donofrio et al. |
| 2010/0114225 A1 | 5/2010 | Imran et al. |
| 2010/0149042 A1 | 6/2010 | Utsi |
| 2010/0161002 A1 * | 6/2010 | Aghassian et al. ............. 607/60 |
| 2010/0168818 A1 | 7/2010 | Barror et al. |
| 2010/0194541 A1 | 8/2010 | Stevenson et al. |
| 2010/0321163 A1 | 12/2010 | Stevenson |
| 2011/0004076 A1 | 1/2011 | Janna et al. |
| 2012/0071942 A1 | 3/2012 | Kamath et al. |
| 2012/0326886 A1 | 12/2012 | Herman et al. |
| 2013/0289666 A1 | 10/2013 | Johnson et al. |

* cited by examiner

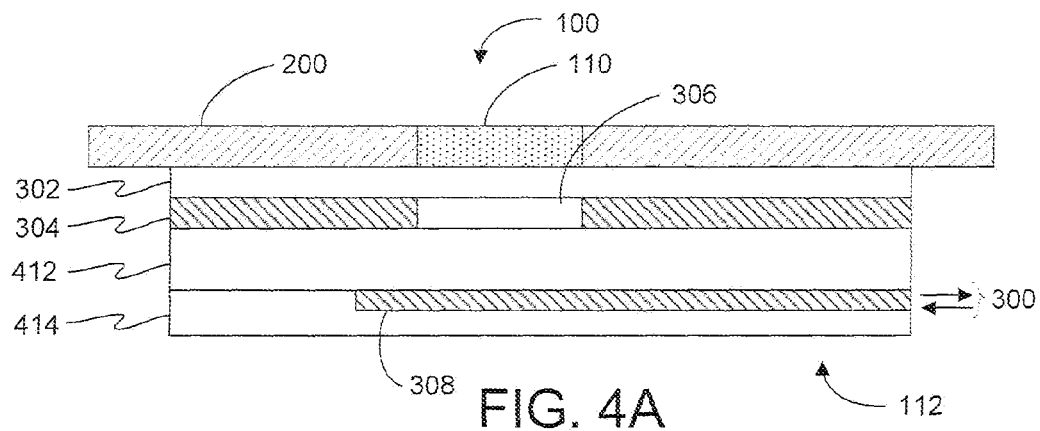
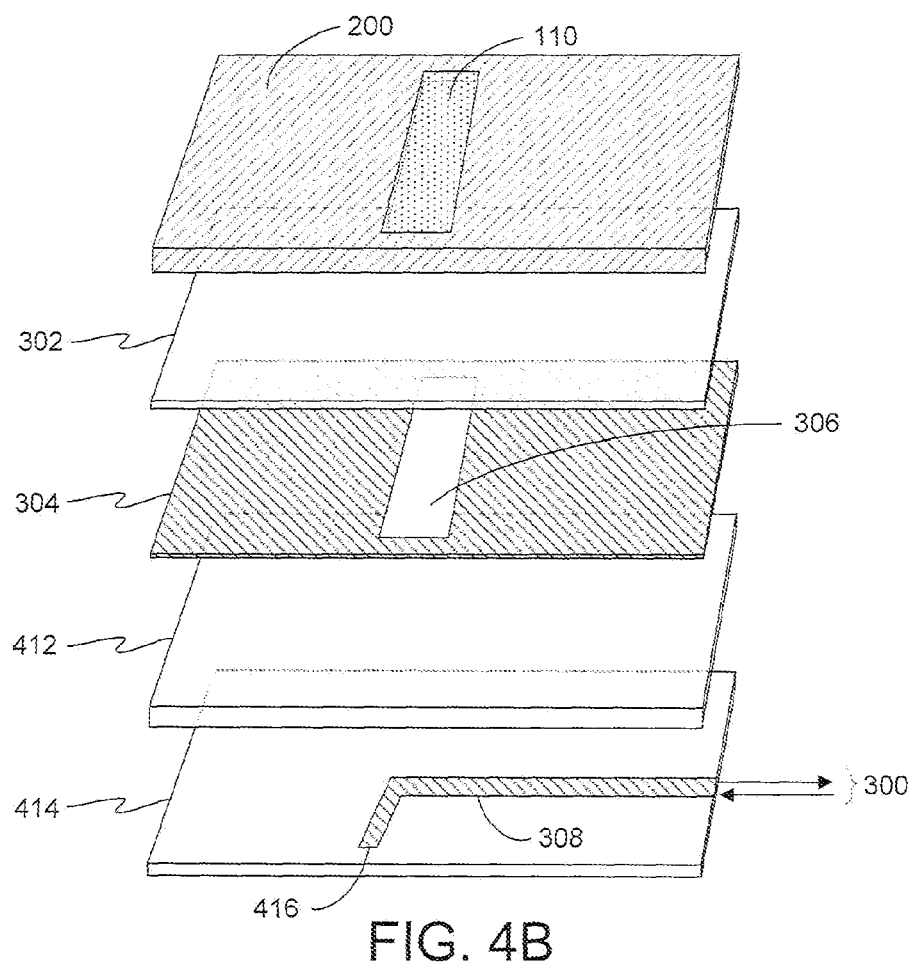

SLOT ANTENNA FOR AN IMPLANTABLE DEVICE

BACKGROUND

The present disclosure relates generally to the field of implantable medical devices. More specifically, the present disclosure relates to a slot antenna in an implantable medical device.

SUMMARY

One embodiment of the disclosure relates to an implantable medical device which includes a case which houses components of the implantable medical device. The implantable medical device includes an inductive coil coupled to a rechargeable battery. The inductive coil may be operative to inductively couple to an external coil and to transfer energy from the external coil to the rechargeable battery to recharge the rechargeable battery. The implantable medical device may include a cutout formed in the case of the implantable medical device and filled with a dielectric material. The cutout may be operative to reduce eddy currents in the case during recharge of the rechargeable battery. The implantable medical device may include a slot antenna disposed within the case. The slot antenna may be operative to communicate with an external device through the cutout in the case.

Another embodiment of the disclosure relates to an implantable medical device which may have a case which houses components of the implantable medical device. The implantable medical device may include a slot antenna disposed within the case. The slot antenna may be operative to communicate with an external device through a cutout in the case. The slot antenna may include a slot formed in a first metal layer above a first dielectric layer. The slot antenna may include a feed line formed in a second metal layer below the first dielectric layer. Further, the slot antenna may include a second dielectric layer formed over the first metal layer and the slot.

One embodiment of the disclosure relates to a method which may include forming a cutout in a metal case of an implantable medical device. The method may also include filling the cutout with a dielectric material to provide a hermetic seal. Further, the method may include disposing a slot antenna within the implantable medical device such that a slot of the slot antenna is aligned with the cutout in the metal case. The first metal layer in which the slot is formed may not be in contact with the metal case.

Another embodiment of the disclosure relates to a method which may include receiving a first inductive recharge signal at a secondary coil of an implantable medical device from a primary coil of an external device. The first inductive recharge signal may be operative to recharge a replenishable power source of the implantable medical device. The method may also include transmitting a first radio frequency signal through a cutout in a case of the implantable medical device from a slot antenna disposed in the implantable medical device to the external device. The first radio frequency signal may have data corresponding to the recharging of the replenishable power source. The first radio frequency signal may be transmitted while the secondary coil receives the first inductive recharge signal.

BRIEF DESCRIPTION OF THE DRAWINGS

The disclosure will become more fully understood from the following detailed description, taken in conjunction with the accompanying drawings.

FIGS. 4A-4B illustrate a side view and a layering view of the implantable medical device, according to an exemplary embodiment.

DETAILED DESCRIPTION OF THE EXEMPLARY EMBODIMENTS

Figure 1:
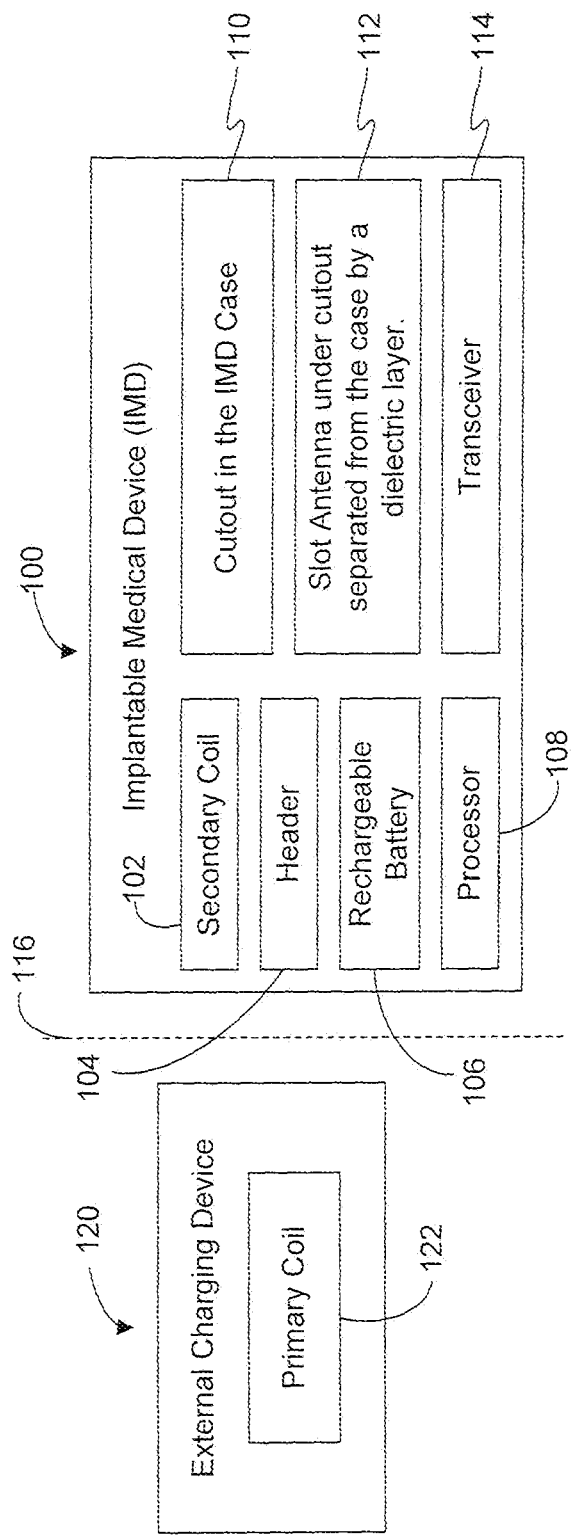
FIG. 1 is a block diagram of the implantable medical device and an external charging device, according to an exemplary embodiment.

Referring to FIG. 1, a block diagram of an implantable medical device (IMD) 100 and an external charging device 120 are shown, according to an exemplary embodiment. The IMD 100 may include a secondary coil 102, a header 104, a rechargeable battery 106, a processor 108, a dielectric filled cutout 110 in the IMD case, a slot antenna 112, and a transceiver 114, according to one exemplary embodiment. The external charging device 120 may include a primary coil 122, according to an exemplary embodiment.

The header 104 may be configured to couple one or more wire leads to the IMD 100. The wire leads may include electrodes for sensing or delivering therapy, such as delivering electrical stimulation to neural tissue. The primary coil 122 of the external charging device 120 may be configured to inductively couple to the secondary coil 102 of the IMD 100 across a tissue barrier 116 of a patient, such as the patient's skin. The primary coil 122 may be configured to induce a current in the secondary coil 102. The secondary coil 102 may be coupled to the rechargeable battery and operative to recharge the rechargeable battery 106 using the induced current. The processor 108 may be configured to monitor the recharging of the rechargeable battery 106 and restrict further recharging once the rechargeable battery 106 is sufficiently charged.

Figure 2:
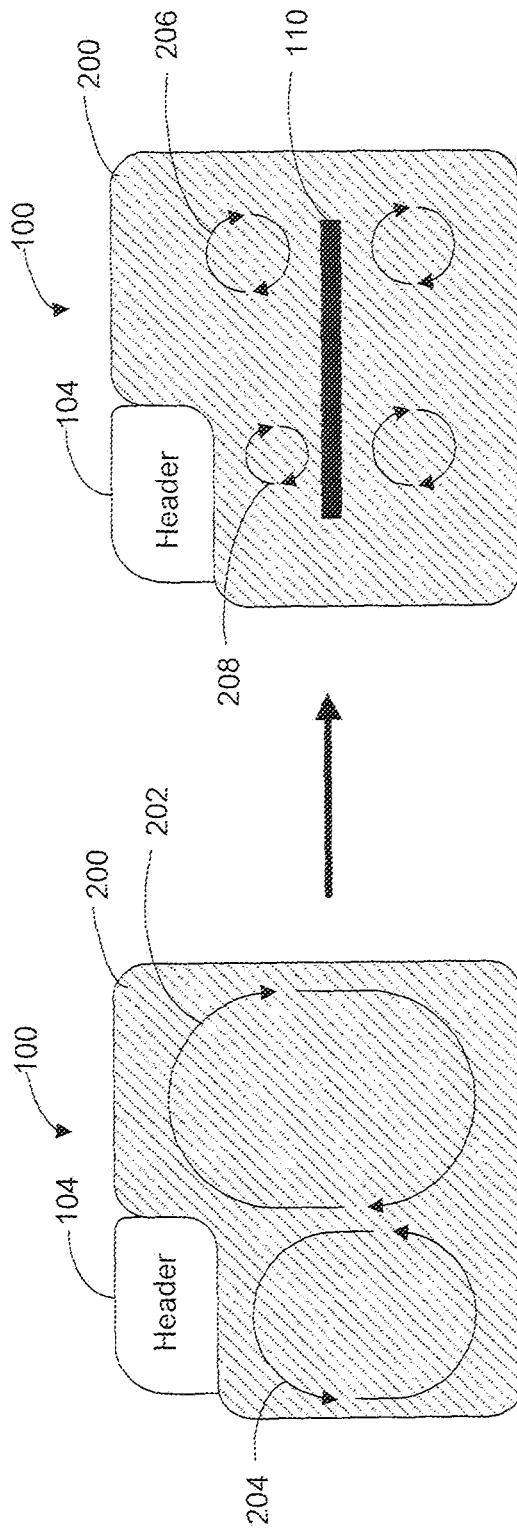
FIGS. 2A-2B illustrate an implantable medical device with large Eddy currents and an implantable medical device with smaller Eddy currents, according to an exemplary embodiment.

The cutout 110 may be one or more cutouts in a conductive case of the IMD 100, as described in FIGS. 2A-2B. The cutout 110 provides resistance to the flow of eddy currents in the conductive case of the IMD 100 that may be induced during recharge of the rechargeable battery 106. The cutout 110 further permits the slot antenna 112 disposed inside the IMD 100 to transmit and receive radio frequency signals. The transceiver 114 may be coupled to the slot antenna 112 and configured to provide radio frequency signals to the slot antenna 112 for transmission and to receive radio frequency signals from the slot antenna 112. In an exemplary embodiment, the transceiver 114 may include a transmitter and a receiver pair. The slot antenna 112 may be separated from the conductive case of the IMD 110 by a dielectric layer.

In some embodiments, the IMD 100 may be configured to transmit and receive radio frequency signals during recharging of the rechargeable battery 106. Further, the IMD 100 may be configured to transmit a radio frequency signal to the external charging device 120. The transmitted signal may be configured to provide information relating to the recharging of the rechargeable battery 106. The information may be used to notify the external device 120 that the rechargeable battery is fully charged, to indicate that the temperature of the IMD 100 has exceeded a tolerance, to assist the external charging device 120 in determining the resonant frequency for recharging, or any other information that may be useful during the recharging process. Providing feedback to the external charging device 120 may increase efficiency of the recharging process, reduce charging time, and increase safety.

Referring to FIGS. 2A and 2B, illustrations of various eddy currents are shown, according to exemplary embodiments. In FIG. 2A, IMD 100 includes the header 104 and a conductive case 200. The conductive case 200 may be made from titanium, stainless steel, or any other suitable conductive material for use as an implantable device case. The conductive case 200 may be configured to house the various components of the IMD 100, such as the secondary coil 102 of FIG. 1, the rechargeable battery 106, the processor 108, and the slot antenna 112. During recharge of the rechargeable battery 106, the flow of eddy currents 202 and 204 may be induced in the conductive case 200 causing heating of the conductive case 200. Excessive heating of the conductive case 200 may result in damage to the surrounding tissue. The flow of eddy currents, and resulting heating of the conductive case 200, may be reduced by providing one or more cutouts in the conductive case 200, such as cutout 110 of FIG. 2B. The cutout 110 may be filled with a dielectric material, such as ceramic. The cutout 110 increases resistance to the flow of eddy currents in the conductive case 200 resulting in reduced flow of eddy currents 206 and 208. The increased resistance to the flow of eddy currents may reduce heating in the conductive case 200. A slot antenna, such as slot antenna 112 of FIG. 1, may be disposed within the conductive case 200 and aligned with the cutout 110 so that the slot antenna 112 may transmit and receive radio frequency signals.

Figure 3:
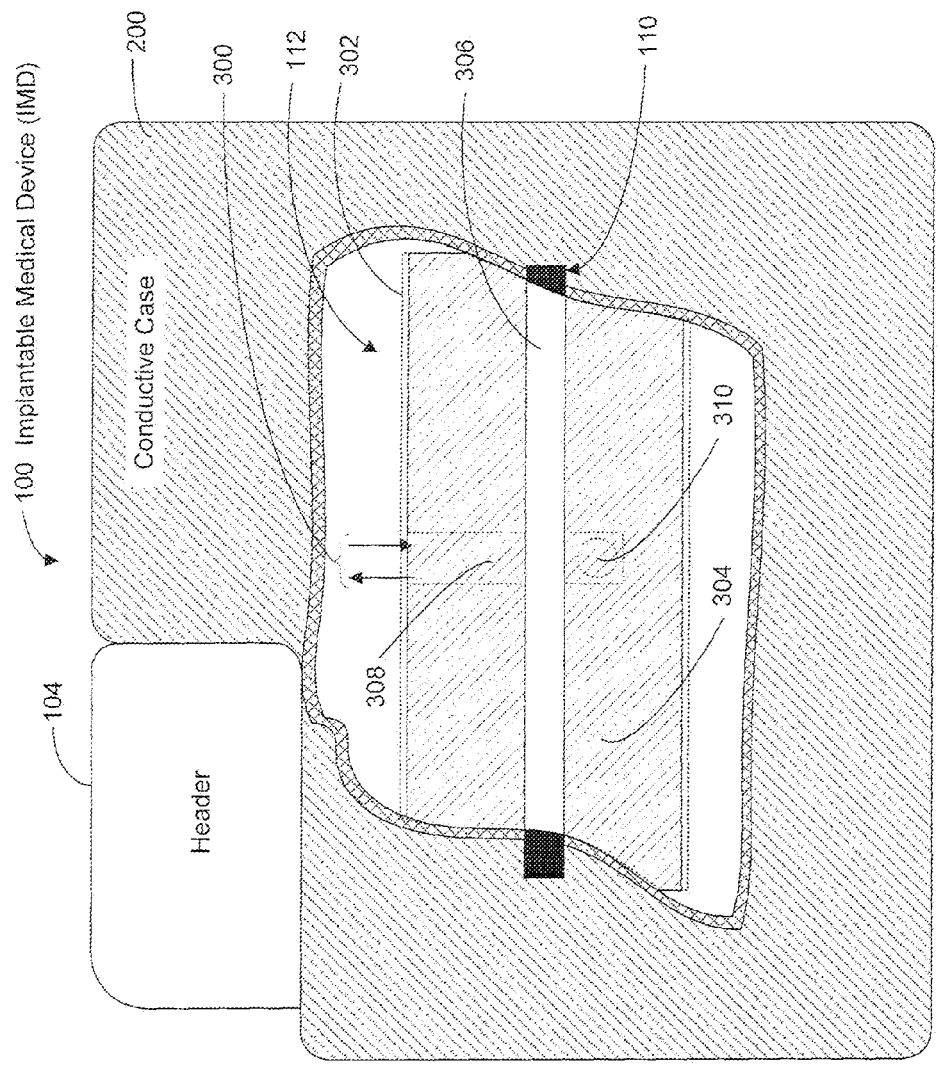
FIG. 3 is a diagram of an implantable medical device, according to an exemplary embodiment.

Referring to FIG. 3, a diagram of an implantable medical device 100 is shown, according to an exemplary embodiment. IMD 100 may include the conductive case 200, the header 104, the cutout 110 filled with a dielectric material, and the slot antenna 112 disposed within the conductive case 200. The slot antenna 112 may include a metal layer 304 and a slot 306 formed by removing a portion of the metal layer 304. A dielectric layer 302 may be provided between the conductive case 200 and the metal layer 304 including the slot 306. The dielectric layer 302 may be an insert provided on the inside wall of the conductive case 200 or it may be formed on the metal layer 304 and the slot 306. The slot antenna 112 may further include a feed line 308 formed in a second metal layer and configured to communicate data 300 using radio frequency signals to and from the slot 306. The slot antenna 112 may include a port coupled to the feed line 308 to facilitate communication between a transceiver and the feed line 308. The feed line 308 may be shorted to the metal layer 304 using a via 310. In another embodiment, instead of shorting the feed line 308 to the metal layer 304, the feed line 308 may include a feed (or stub) that creates a virtual short at certain frequencies as will be discussed further in FIG. 4B. The slot antenna 112 may be formed from a PC board having at least two metal layers. In another exemplary embodiment, dielectric layer 302 may be formed over metal layer 304 and the slot 306 using chemical vapor deposition (CVD), including plasma enhanced CVD and low-pressure CVD, atomic layer deposition (ALD), and physical layer deposition (PLD). Any other type of deposition process may be used to form the dielectric layer 302 without departing from the scope of the present disclosure.

Referring to FIGS. 4A-4B, a side-view diagram of a portion of the IMD 100, including the slot antenna 112, is shown, according to an exemplary embodiment. The IMD 100 includes a conductive case 200 having a cutout 110 filled with a dielectric material, such as ceramic material. The IMD 100 may be configured to house the slot antenna 112 having a slot 306 aligned with the cutout 110. The slot antenna 112 includes a metal layer 304 provided on a dielectric substrate 412. A portion of the metal layer 304 is removed to form a slot 306. The slot 306 may be filled with a dielectric material or left empty.

A dielectric layer 302 may be provided between the conductive case 200 and the metal layer 304 including the slot 306. The dielectric layer 302 may be an insert provided on the inside wall of the conductive case 200 or it may be deposited, grown, or otherwise formed on the metal layer 304 and the slot 306. The slot antenna 112 may further include a feed line 308 formed in a second metal layer and configured to communicate data 300 using radio frequency signals to and from the slot 306. The feed line 308 may include a feed 416 (or stub) that creates a virtual short at certain frequencies. The feed 416 length may be sized to be equal to approximately one quarter of the wavelength (e.g., $\lambda/4$) of the radio frequency signals transmitted by the slot antenna 112; however, various other lengths may be used. The width and height of the feed line 308 and the feed 416 may be determined based on the impedance of the conductive material used.

While the feed 416 of FIG. 4B is at a ninety degree angle with respect to the feed line 308, the feed 416 may extend at other angles including one-hundred and eighty degrees from the feed line 308 to form a linear metal trace. In another embodiment, the slot antenna may include at least a third metal layer and the feed 416 may extend to the third metal layer using a conductive via. Further, the feed 416 may be extended to multiple metal layers using multiple conductive vias. The feed 416 may also form a T-shape with respect to the feed line 308. A dielectric layer 414 may be provided over the second metal layer, including the feed line 308 to insulate the slot antenna 112 from other components housed within the IMD 100.

In some embodiments, the slot antenna 112 may be formed using a PC board having at least two conductive layers. The conductive layers, such as metal layer 304 and the second metal layer in which the feed line 308 is formed, may be made from copper. The dielectric substrate may be made selected from a variety of dielectric materials, including, but not limited to, Teflon, FR-1, FR-2, FR-3, FR-4, FR-5, FR-6, CEM-1, CEM-2, CEM-3, CEM-4, CEM-5, and G-10. In some embodiments, the dielectric layer 412 may be a flexible plastic substrate used to form a flexible printed circuit. The flexible plastic substrate may be a polyimide material, polyether ether ketone (PEEK) material, or any other suitable material.

In some embodiments, the slot antenna 112 may be formed on a multi-layered PC board such that various electronic components used by the IMD 100 may be provided on one or more of the layers of the multi-layered PC board.

Figure 5A:
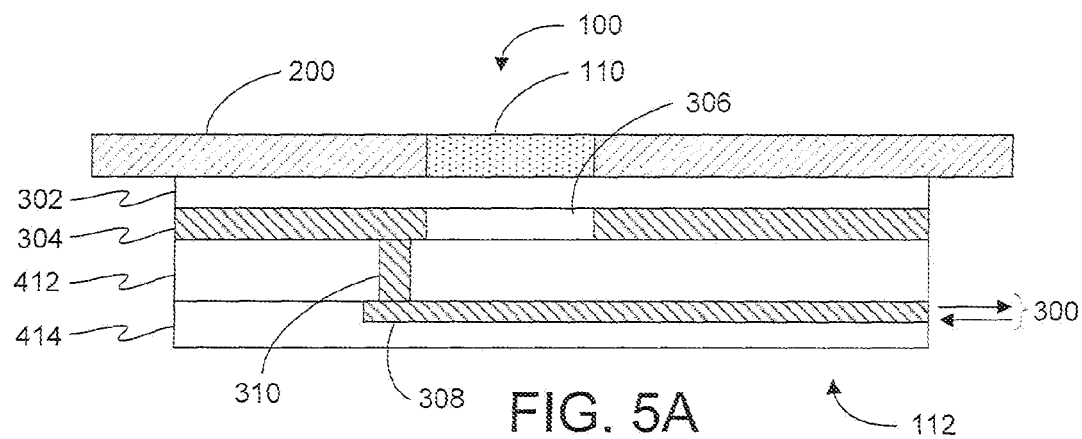
FIGS. 5A-5B illustrate a side view and a layering view of the implantable medical device, according to an exemplary embodiment.
Figure 5B:
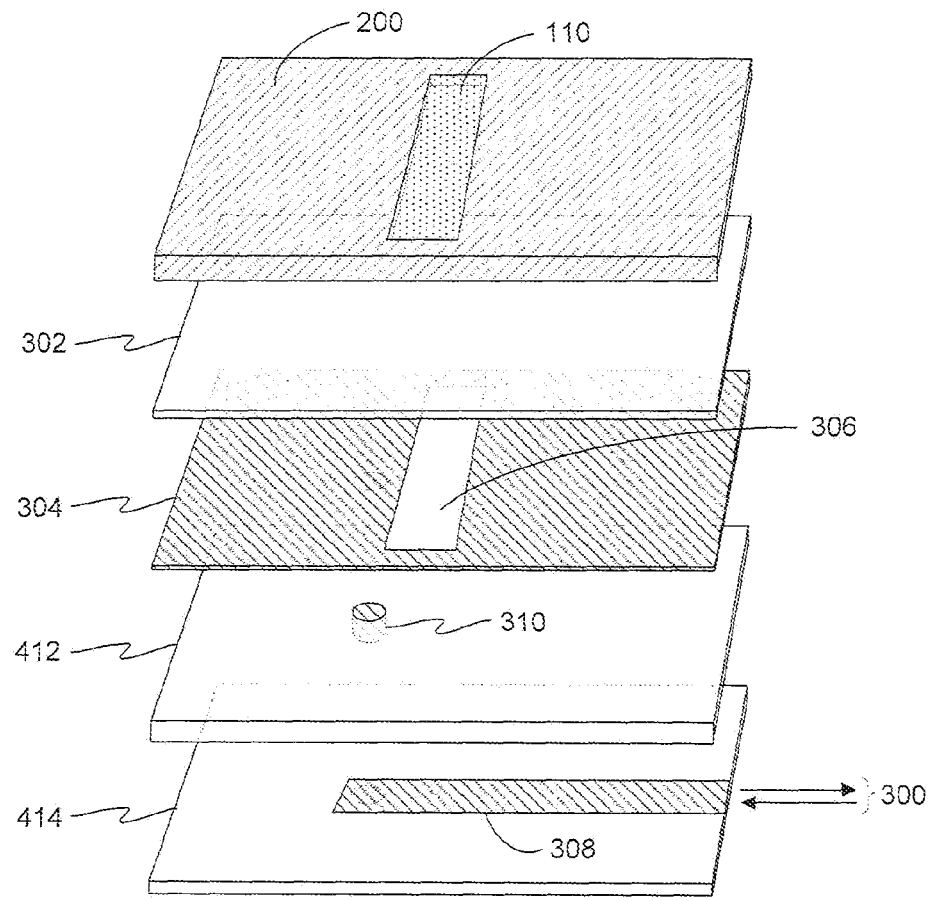

Referring to FIGS. 5A-5B, another side-view diagram of a portion of IMD 100 is shown, according to an exemplary embodiment. As previously described with respect to FIGS. 4A-4B, the IMD 100 may include a conductive case 200, a cutout 110 in the conductive case 200 filled with a dielectric material, a dielectric layer 302, a metal layer 304 including a slot 306 formed by removing a portion of the metal layer 304, a dielectric substrate 412, a feed line 308, and a dielectric layer 414. The feed line 308 may be configured to communicate data 300 using radio frequency signals to and from the slot 306. FIGS. 5A-5B further include a conductive via 310 for coupling the feed line 308 to the metal layer 304. Coupling the feed line 308 to the metal layer 304 allows for a more compact design by eliminating the need to form a virtual short with the feed 416 (or stub) of FIG. 4B.

Figure 6A:
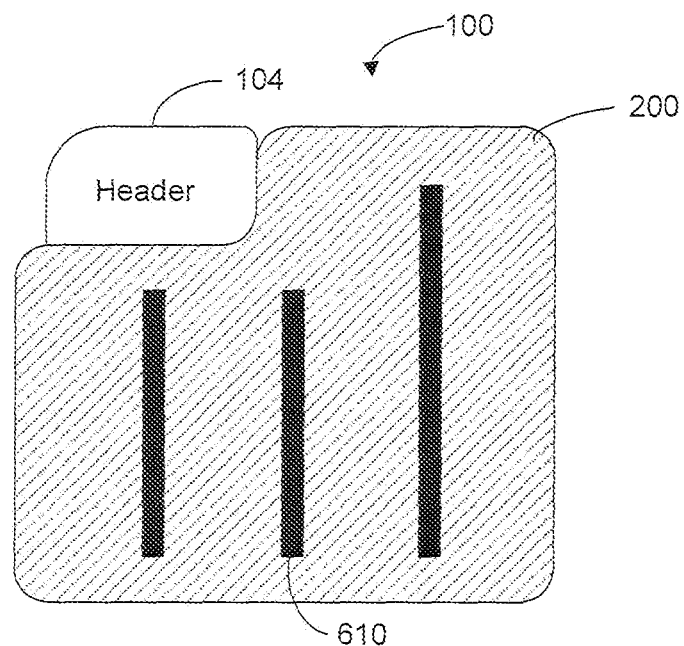
FIGS. 6A-6B illustrate an implantable medical device having multiple cutouts, according to an exemplary embodiment.
Figure 6B:
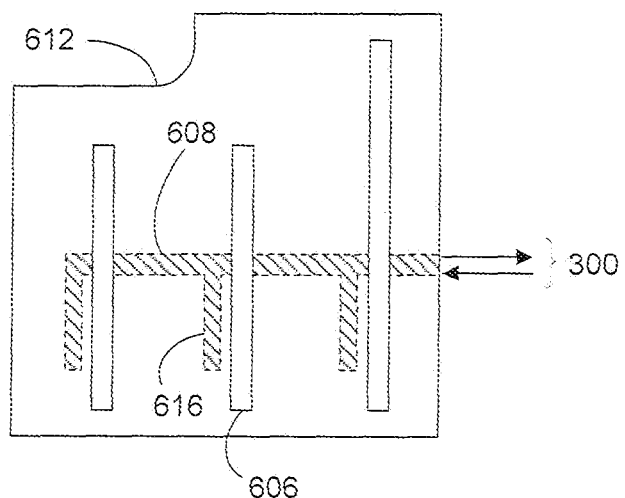

Referring to FIGS. 6A-6B, an IMD 100 having multiple cutouts 610 is shown, according to an exemplary embodiment. The cutouts 610 in the conductive case 200 may be spaced apart to maximize the reduction of the flow of eddy currents. The cutouts 610 may be filled with a dielectric material, such as ceramic. A slot antenna 612 may be disposed within the conductive case 200 such that slots 606 of the slot antenna 612 are aligned with the cutouts 610. The slot antenna 612 may include the layers shown in FIGS. 4A-4B and 5A-5B. For simplicity, only the slots 606, the feed line 608, and feeds 616 are shown. The slots 606 are formed by removing portions of a metal layer. The feed line 608 may be configured to communicate data 300 using radio frequency signals to and from the slots 606. The feed line 608 and the metal layer in which the slots 606 are formed are separated by a dielectric layer or substrate. The feed line 608 passes under each slot and may include feeds 616 which may be sized have a length of approximately one quarter of the wavelength (e.g., λ/4) of the radio frequency signals transmitted by the slot antenna 612; however, various other lengths may be used. In some embodiments, one or more vias may be used to couple the feed line 608 to the metal layer in which the slots 606 are formed. Any number of cutouts 610 may be used. Further, the cutouts 610 may be any shape or design (e.g., curved, jagged, angled, tapered width), or form any pattern, including a radial pattern.

Figure 7A:
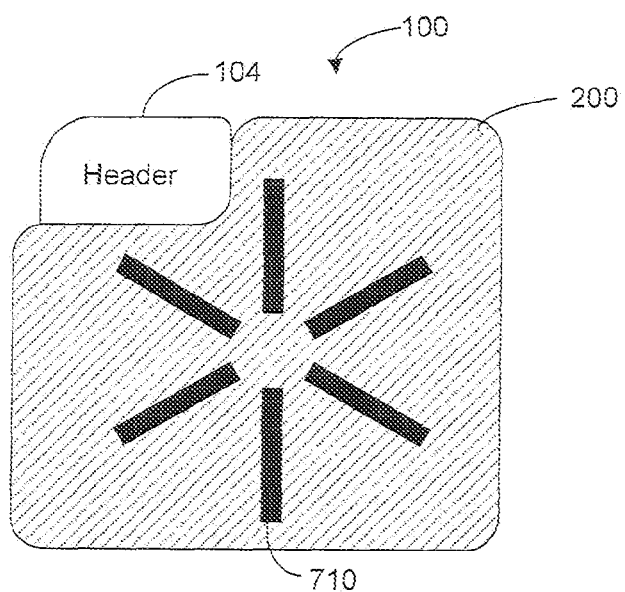
FIGS. 7A-7C illustrate an implantable medical device having multiple cutouts, according to an exemplary embodiment.
Figure 7B:
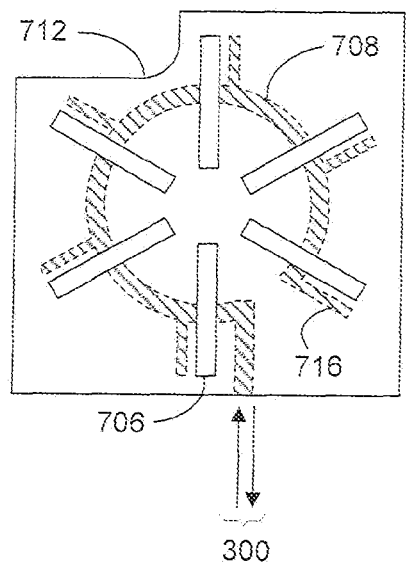
Figure 7C:
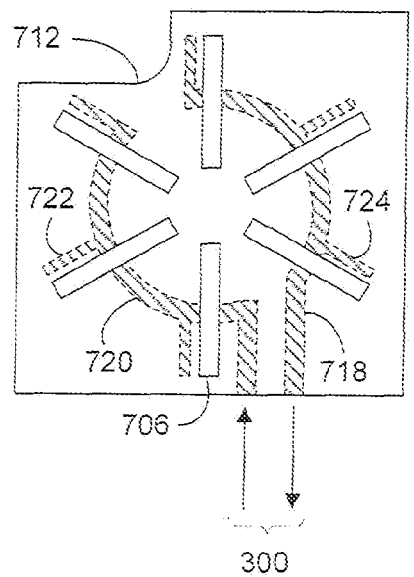

Referring to FIGS. 7A-7C, another implantable medical device 100 having multiple cutouts 710 is shown, according to an exemplary embodiment. The cutouts 710 in the conductive case 200 form a radial pattern. In some embodiments, the radial pattern may be located in a center or an off-center location. Further, the radial pattern may be centered on the portion of the conductive case 200 covering the secondary coil 102 of FIG. 1. The cutouts 710 may be filled with a dielectric material, such as ceramic. In some embodiments, the number of cutouts 710, and corresponding slots 706, forming the radial pattern may be fewer than six, while in other embodiments there may be more than six in the radial pattern. The feed line 708 may be configured to communicate data 300 using radio frequency signals to and from the slot 706. A slot antenna 712 may be disposed within the conductive case 200 such that slots 706 of the slot antenna 712 are aligned with the cutouts 710. The slot antenna 712 of FIGS. 7B-7C may include the layers shown in FIGS. 4A-4B and 5A-5B. For simplicity, only the slots 706, the feed line 708, and the feeds 716 are shown. The slots 706 are formed by removing portions of a metal layer, such as metal layer 304. The feed line 708 and the metal layer, in which the slots 706 are formed, are separated by a dielectric layer or substrate. The feed line 708 passes under the slots to form a circular pattern and may include feeds 716 which may be sized to have a length of approximately one quarter of the wavelength (e.g., λ/4) of the radio frequency signals transmitted by the slot antenna 712; however, various other lengths may be used. In some embodiments, one or more vias may be used to couple the feed line 708 to the metal layer in which the slots 706 are formed. The feed line 708 of FIG. 7B may be used to both transmit and receive data 300.

In some embodiments, the feed line 720 of FIG. 7C may be used to transmit data 300 while the feed line 718 may be used to receive data 300. The feed lines 720 and 718 each form a semi circular pattern. The feed line 720 may include feeds 722 configured for transmitting data 300. In some embodiments, one or more of the feeds 722 may be replaced with conductive vias, such as the conductive via 310 of FIGS. 5A-5B. The feed line 718 may include feeds 724 configured for receiving data 300. In some embodiments, one or more of the feeds 724 may be replaced with conductive vias, such as the conductive via 310 of FIGS. 5A-5B.

Further, the cutouts 710, and corresponding slots 706, may be any shape or design (e.g., curved, jagged, angled, tapered width, U-shaped, L-shaped, T-shaped, dog bone shaped). The length of each of the cutouts 706 need not be the same. The slots 706 need not be as long as the cutouts 710 or the same width.

Figure 8:
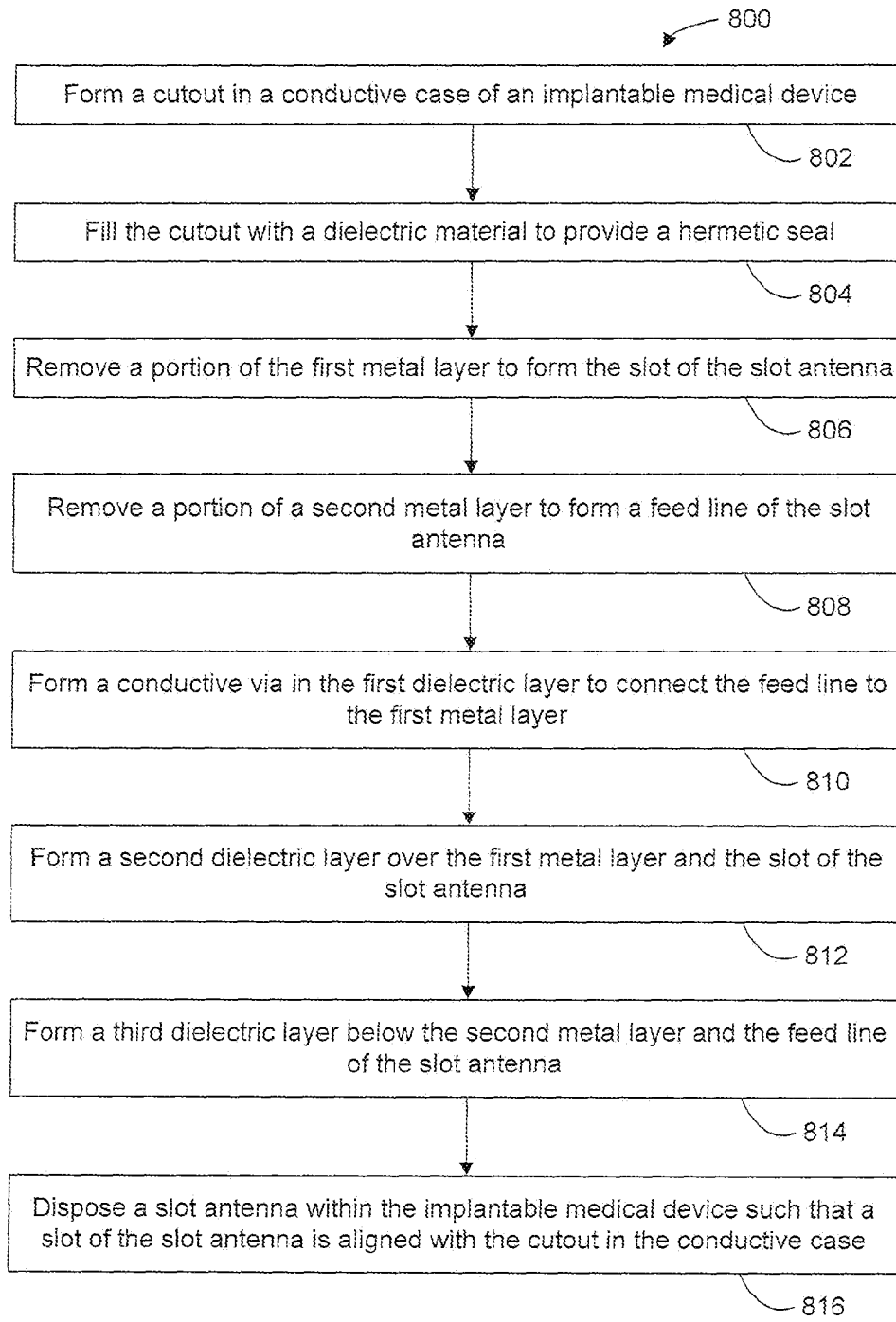
FIG. 8 is a process flow chart for a method of manufacturing the slot antenna, according to an exemplary embodiment.

Referring to FIG. 8, a process flow chart for a method 800 of manufacturing the slot antenna is shown, according to an exemplary embodiment. The method 800 may include forming a cutout in a conductive case of an implantable medical device, at 802. The case may be made from a metallic material, such as titanium or stainless steal. In an alternative embodiment, the case may be non-metallic. The method 800 may also include filling the cutout with a dielectric material to provide a hermetic seal, at 804. The dielectric material may be a ceramic material or any other dielectric material suitable to form a hermetic seal. The method 800 may include removing a portion of a first metal layer to form a slot of the slot antenna, at 806. In an exemplary embodiment, the first metal layer may be disposed above a first dielectric layer or substrate. The first metal layer may be made from copper. The method 800 may include removing a portion of a second metal layer to form a feed line of the slot antenna, at 808. In an exemplary embodiment, the second metal layer may be disposed below the first dielectric layer or substrate and may also be made from copper. The method 800 may also include forming a conductive via in the first dielectric layer to connect the feed line to the first metal layer, at 810. The method 800 may include forming a second dielectric layer over the first metal layer and the slot of the slot antenna, at 812. The method 800 may include forming a third dielectric layer below the second metal layer and the feed line of the slot antenna, at 814. The method 800 may include disposing a slot antenna within the implantable medical device such that the slot of the slot antenna is aligned with the cutout in the implantable medical case, at 806. In an exemplary embodiment, the first metal layer in which the slot is formed may not be in contact with the conductive case.

Figure 9:
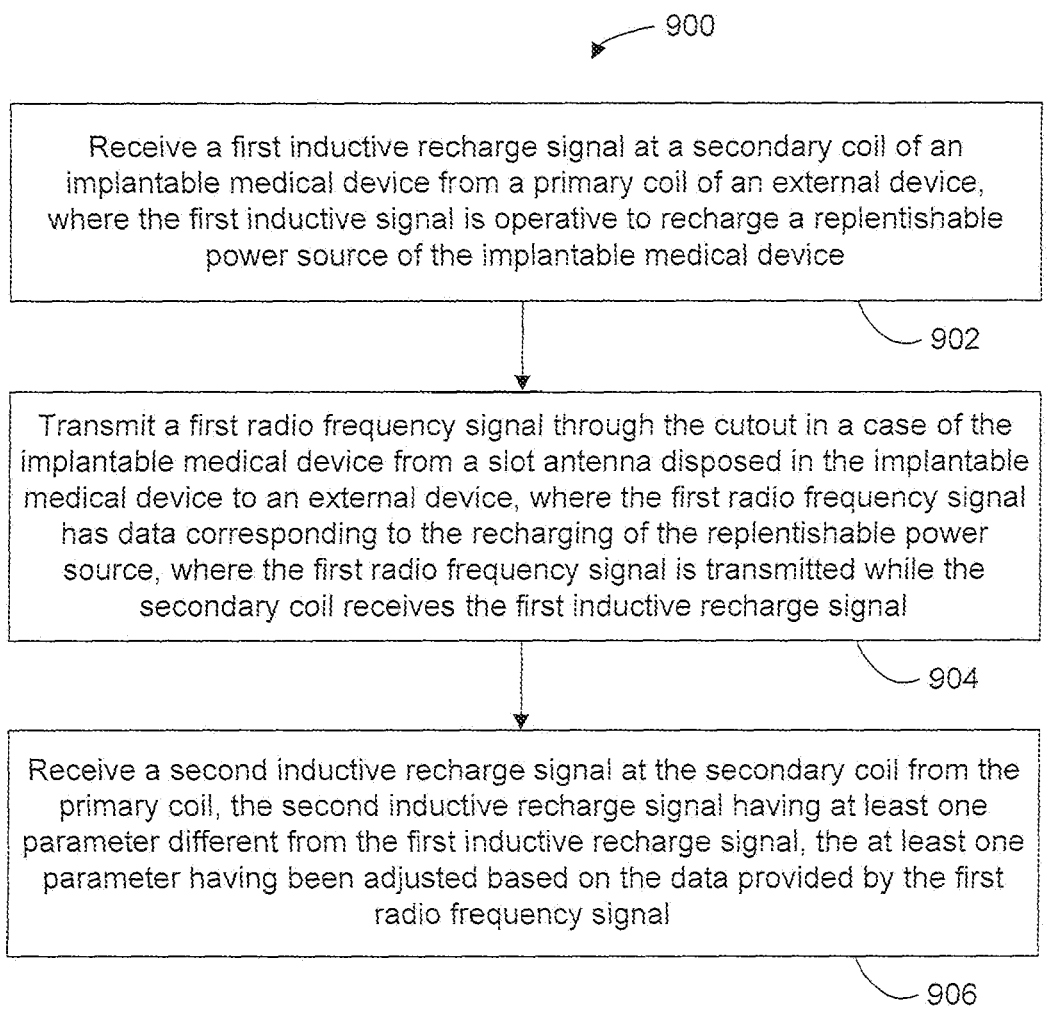
FIG. 9 is a process flow chart for a method of communicating via the slot antenna during the recharging process, according to an exemplary embodiment.

Referring to FIG. 9, a process flow chart for a method 900 of communicating via the slot antenna during the recharging process is shown, according to an exemplary embodiment. The method 900 may include receiving a first inductive recharge signal at a secondary coil of the implantable medical device from a primary coil of an external device, at 902. In an exemplary embodiment, the first inductive recharge signal may be operative to recharge a replenishable power source of the implantable medical device, such as a rechargeable battery. The method 900 may also include transmitting a first radio frequency signal through a cutout in a case of the implantable medical device from a slot antenna disposed in the implantable medical device to an external device, and 904. In an exemplary embodiment, the first radio frequency signal has data corresponding to the charging of the replenishable power source and the first radio frequency signal may be transmitted while the secondary coil receives the first inductive recharge signal. The method 900 may include receiving a second inductive recharge signal at the secondary coil from the primary coil, where the second inductive recharge signal has at least one parameter different from the first inductive recharge signal, the at least one parameter having been adjusted based on the data provided by the first radio frequency signal, at 906. In this manner, a recharging feedback loop may be provided to the external charging device to maintain safety and efficiency during the recharging process. In an exemplary embodiment, the recharging feedback loop may be utilized to monitor the recharging process to maintain the temperature of the any portion of the implantable medical device. In some embodiments, the recharge feedback loop may be used to determine the resonant frequency for the recharge process and to assist in maintaining the inductive recharge signal at or near the resonant frequency during the recharge process.

Using the data provided by the recharging feedback loop, the external recharging device may be configured to monitor the effects of the inductive recharging signal on the implantable medical device and its components, and adjust the inductive recharging signal to improve the safety and efficiency of the recharge process. In an exemplary embodiment, the external recharging device may be configured to monitor a temperature of the implantable medical device and to adjust the parameters of the inductive recharging signal based on the temperature. For example, the external recharging device may attempt to reduce the temperature of the implantable medical device by discontinuing the recharge process, reducing the duty cycle of the inductive recharge signal, adjusting the frequency of the inductive recharge signal to more closely match the resonant frequency, and reducing the magnitude of the inductive recharge signal. The external recharging device, or any other external computing device configured to communicate with the implantable medical device, may use the data to generate generating a status report or a history report of the implantable medical device. The status report and history report may include temperature data, frequency data, or any other data provided by the implantable medical device. The external recharging device, or any other external computing device configured to communicate with the implantable medical device, may also be configured to generate a recharging request based on the monitoring of the implantable medical device. For example, the external device may notify the user that a power level of the rechargeable battery has dropped below a power threshold and is in need of recharging.

Although the description above contains many specificities, these specificities are utilized to illustrate some of the exemplary embodiments of this disclosure and should not be construed as limiting the scope of the disclosure. The scope of this disclosure should be determined by the claims, their legal equivalents and the fact that it fully encompasses other embodiments which may become apparent to those skilled in the art. A method or device does not have to address each and every problem to be encompassed by the present disclosure. All structural, chemical and functional equivalents to the elements of the below-described disclosure that are known to those of ordinary skill in the art are expressly incorporated herein by reference and are intended to be encompassed by the present claims. A reference to an element in the singular is not intended to mean one and only one, unless explicitly so stated, but rather it should be construed to mean at least one. No claim element herein is to be construed under the provisions of 35 U.S.C. §112, sixth paragraph, unless the element is expressly recited using the phrase "means for." Furthermore, no element, component or method step in the present disclosure is intended to be dedicated to the public, regardless of whether the element, component or method step is explicitly recited in the claims.

The disclosure is described above with reference to drawings. These drawings illustrate certain details of specific embodiments that implement the systems and methods and programs of the present disclosure. However, describing the disclosure with drawings should not be construed as imposing on the disclosure any limitations that may be present in the drawings. The present disclosure contemplates methods, systems and program products on any machine-readable media for accomplishing its operations. The embodiments of the present disclosure may be implemented using an existing computer processor, or by a special purpose computer processor incorporated for this or another purpose or by a hardwired system.

As noted above, embodiments within the scope of the present disclosure include program products comprising machine-readable media for carrying or having machine-executable instructions or data structures stored thereon. Such machine-readable media can be any available media which can be accessed by a general purpose or special purpose computer or other machine with a processor. By way of example, such machine-readable media can comprise RAM, ROM, EPROM, EEPROM, CD ROM or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. The disclosure may be utilized in a non-transitory media. When information is transferred or provided over a network or another communications connection (either hardwired, wireless, or a combination of hardwired or wireless) to a machine, the machine properly views the connection as a machine-readable medium. Thus, any such a connection is properly termed a machine-readable medium. Combinations of the above are also included within the scope of machine-readable media. Machine-executable instructions comprise, for example, instructions and data which cause a general purpose computer, special purpose computer, or special purpose processing machines to perform a certain function or group of functions.

Embodiments of the disclosure are described in the general context of method steps which may be implemented in one embodiment by a program product including machine-executable instructions, such as program code, for example, in the form of program modules executed by machines in networked environments. Generally, program modules include routines, programs, objects, components, data structures, etc., that perform particular tasks or implement particular abstract data types. Machine-executable instructions, associated data structures, and program modules represent examples of program code for executing steps of the methods disclosed herein. The particular sequence of such executable instructions or associated data structures represent examples of corresponding acts for implementing the functions described in such steps.

Embodiments of the present disclosure may be practiced in a networked environment using logical connections to one or more remote computers having processors. Logical connections may include a local area network (LAN) and a wide area network (WAN) that are presented here by way of example and not limitation. Such networking environments are commonplace in office-wide or enterprise-wide computer networks, intranets and the Internet and may use a wide variety of different communication protocols. Those skilled in the art will appreciate that such network computing environments will typically encompass many types of computer system configurations, including personal computers, hand-held devices, multi-processor systems, microprocessor-based or programmable consumer electronics, network PCs, servers, minicomputers, mainframe computers, and the like. Embodiments of the disclosure may also be practiced in distributed computing environments where tasks are performed by local and remote processing devices that are linked (either by hardwired links, wireless links, or by a combination of hardwired or wireless links) through a communications network. In a distributed computing environment, program modules may be located in both local and remote memory storage devices.

An exemplary system for implementing the overall system or portions of the disclosure might include a general purpose computing device in the form of a computer, including a processing unit, a system memory, and a system bus that couples various system components including the system memory to the processing unit. The system memory may include read only memory (ROM) and random access memory (RAM). The computer may also include a magnetic hard disk drive for reading from and writing to a magnetic hard disk, a magnetic disk drive for reading from or writing to a removable magnetic disk, and an optical disk drive for reading from or writing to a removable optical disk such as a CD ROM or other optical media. The drives and their associated machine-readable media provide nonvolatile storage of machine-executable instructions, data structures, program modules, and other data for the computer. It should be noted that although the flowcharts provided herein show a specific order of method steps, it is understood that the order of these steps may differ from what is depicted. Also two or more steps may be performed concurrently or with partial concurrence. Such variation will depend on the software and hardware systems chosen and on designer choice. It is understood that all such variations are within the scope of the disclosure. Likewise, software and web implementations of the present disclosure could be accomplished with standard programming techniques with rule based logic and other logic to accomplish the various database searching steps, correlation steps, comparison steps and decision steps. It should also be noted that the word "component" as used herein and in the claims is intended to encompass implementations using one or more lines of software code, and/or hardware implementations, and/or equipment for receiving manual inputs.

The foregoing description of embodiments of the disclosure have been presented for purposes of illustration and description. It is not intended to be exhaustive or to limit the disclosure to the precise form disclosed, and modifications and variations are possible in light of the above teachings or may be acquired from practice of the disclosure. The embodiments were chosen and described in order to explain the principals of the disclosure and its practical application to enable one skilled in the art to utilize the disclosure in various embodiments and with various modifications as are suited to the particular use contemplated.

What is claimed is:

1. An implantable medical device having a case configured to house components of the implantable medical device, the implantable medical device comprising:
   an inductive coil coupled to a rechargeable battery, the inductive coil operative to inductively couple to an external coil and to transfer energy from the external coil to the rechargeable battery to recharge the rechargeable battery;
   a cutout formed in the case of the implantable medical device and filled with a dielectric material, wherein the cutout is operative to reduce eddy currents in the case during recharge of the rechargeable battery; and
   a slot antenna disposed within the case, the slot antenna operative to communicate with an external device through the cutout in the case;
   wherein the slot antenna comprises: a first dielectric layer; a slot formed in a first metal layer above the first dielectric layer; and a feed line formed in a second metal layer below the first dielectric layer.

2. The implantable medical device of claim 1, further comprising:
   a dielectric layer positioned between the slot antenna and the case.

3. The implantable medical device of claim 2, wherein the dielectric layer is formed on the slot antenna.

4. The implantable medical device of claim 1, wherein the slot antenna further comprising:
   a metal via formed in the first dielectric layer, the metal via configured to couple the feed line to the first metal layer.

5. The implantable medical device of claim 4, further comprising:
   a second dielectric layer formed over the first metal layer and the slot.

6. The implantable medical device of claim 4, further comprising:
   a third dielectric layer formed below the second metal layer.

7. The implantable medical device of claim 1, wherein the dielectric material is ceramic.

8. The implantable medical device of claim 1, wherein the slot antenna is operative to communicate with the external device during recharge of the rechargeable battery.

9. An implantable medical device having a case configured to house components of the implantable medical device, the implantable medical device comprising:
   a slot antenna disposed within the case, the slot antenna operative to communicate with an external device through a cutout in the case, the slot antenna further comprising:
   a slot formed in a first metal layer above a first dielectric layer;
   a feed line formed in a second metal layer below the first dielectric layer; and
   a second dielectric layer formed over the first metal layer and the slot.

10. The implantable medical device of claim 9, wherein the slot antenna further comprising:
    a metal via formed in the first dielectric layer, the metal via configured to couple the feed line to the first metal layer.

11. The implantable medical device of claim 9, wherein the case includes a plurality of cutouts and the slot antenna includes a plurality of slots formed in the first metal layer, wherein the plurality of slots are approximately aligned to the plurality of cutouts in the case.

12. The implantable medical device of claim 11, wherein the plurality of cutouts and the corresponding plurality of slots are configured in a radial pattern, wherein the feed line formed in the second layer is curved to form a circular or a semi-circular shape, wherein the feed line is configured to pass under two or more of the plurality of slots.

13. The implantable medical device of claim 9, further comprising:
    a transmitter coupled to the feed line; and
    a receiver coupled to the feed line;

wherein the feed line is operative to provide radio frequency current from the transmitter to the slot and to provide radio frequency signals received at the slot to the receiver.

14. The implantable medical device of claim 9, wherein the first dielectric layer is a printed circuit board.

* * * * *